United States Patent [19]

Gardner

[11] 4,097,480
[45] Jun. 27, 1978

[54] 2,2-DIMETHYL-7-AMINE-ALKOXY-4-ARYL-TETRA-HYDROQUINALINE DERIVATIVES

[75] Inventor: Derek Victor Gardner, Bishops Stortford, England

[73] Assignee: Beecham Group Limited, United Kingdom

[21] Appl. No.: 691,866

[22] Filed: Jun. 1, 1976

[30] Foreign Application Priority Data

Jul. 28, 1975 United Kingdom .............. 31426/75

[51] Int. Cl.$^2$ .................... C07D 215/20; A61K 31/47
[52] U.S. Cl. .......................... 260/286 R; 260/283 SY; 260/283 CN; 260/287 T; 260/288 R; 260/289 H; 424/258
[58] Field of Search ...................... 260/288 R, 286 R; 424/258

[56] References Cited

U.S. PATENT DOCUMENTS

| 1,587,073 | 6/1926 | Hahl | 260/288 R |
| 3,049,510 | 8/1962 | Harris | 260/288 R |

OTHER PUBLICATIONS

Hartmann et al.; Chem. Abst. vol. 26; pp. 3877–3878, (1932) (Abstract of U.S. Pat. No. 1,860,286).
Chem. Abst. vol. 26, p. 3624 (1932), (abstract of German Pat. No. 547,082).

*Primary Examiner*—Donald G. Daus
*Assistant Examiner*—Mary Vaughn
*Attorney, Agent, or Firm*—Jacobs & Jacobs

[57] ABSTRACT

Compounds of the formula (I):

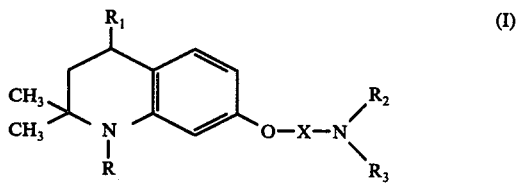

and salts thereof wherein X is a group:

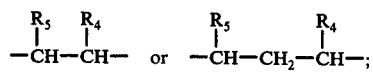

R is hydrogen, methyl or ethyl; $R_1$ is phenyl or naphthyl or phenyl substituted by fluorine, chlorine, bromine, methyl, methoxy or trifluoromethyl; $R_2$ is hydrogen or methyl; $R_3$ is hydrogen, methyl, ethyl or benzyl; $R_4$ is hydrogen or methyl; and $R_5$ is hydrogen or methyl; have been found to be mood modifying agents and anorexic agents.

9 Claims, No Drawings

2,2-DIMETHYL-7-AMINE-ALKOXY-4-ARYLTETRA-HYDROQUINALINE DERIVATIVES

BACKGROUND TO THE INVENTION

United States application Ser. No. 599,694 discloses inter alia that compounds of the formula (II):

(II)

and salts thereof wherein X is an alkylene group of 2-4 carbon atoms; $A_1$ is an aryl group and $A_2$ and $A_3$ are each a hydrogen atom or $C_{1-6}$ alkyl groups; possess mood-modifying and anorexia inducing activity.

There has now been discovered another distinct group of compounds related to those of formula (II) which have useful activity as anorexic agents and mood-modifying agents.

DESCRIPTION OF THE INVENTION

The present invention provides compounds of the formula (I):

(I)

and salts thereof wherein X is a group:

$$-\overset{R_5}{\underset{|}{C}H}-\overset{R_4}{\underset{|}{C}H}- \quad \text{or} \quad -\overset{R_5}{\underset{|}{C}H}-CH_2-\overset{R_4}{\underset{|}{C}H}-;$$

R is hydrogen, methyl or ethyl; $R_1$ is phenyl or naphthyl or phenyl substituted by fluorine, chlorine, bromine, methyl, methoxy or trifluoromethyl; $R_2$ is hydrogen or methyl; $R_3$ is hydrogen, methyl, ethyl or benzyl; $R_4$ is hydrogen or methyl; and $R_5$ is hydrogen or methyl.

Suitably R is hydrogen.

Suitably $R_1$ is phenyl substituted by fluorine, chlorine or trifluoromethyl.

Suitably $R_2$ is methyl.

Suitably $R_3$ is hydrogen or methyl.

Preferably $R_3$ is methyl.

Suitably $R_4$ and $R_5$ are each hydrogen.

A particularly suitable value for the $O-X-NR_2R_3$ group is the $-O-CH_2-CH_2-N(CH_3)_2$ group.

Preferred compounds of this invention include those of formula (III):

(III)

wherein $R_6$ is hydrogen, fluorine, chlorine or trifluoromethyl; and $R_7$ is hydrogen or methyl.

Suitably $R_6$ is trifluoromethyl, for example a 3- or 4-trifluoromethyl group.

Most suitably $R_7$ is methyl.

Since the compounds of this invention are nitrogenous bases they are able to form acid addition salts in conventional manner. Normally, such salts are those formed from pharmaceutically acceptable organic or inorganic acids such as citric, acetic, propionic, benzoic, lactic, tartaric, mandelic, succinic, oleic, glutaric, gluconic, methanesulphonic, toluenesulphonic, sulphuric, phosphoric, hydrobromic or hydrochloric acid.

Compounds within the formula (I) affect the central nervous system. Thus depending on the dosage used, certain compounds of the formula (I) are able to produce anorexic or mood modifying effects in mammals.

Accordingly, in one of its aspects the present invention provides pharmaceutical compositions which comprise a compound of this invention together with a pharmaceutically acceptable carrier.

Normally, the compositions of this invention are adapted for oral administration to humans although compositions adapted for parenteral administration are also envisaged.

The most suitable dosage forms are unit dosage forms such as tablets, capsules, sachets and the like which contain a predetermined quantity of active material.

Such unit dosage forms normally contain from 0.05 to 200 mg. of active material and may be taken once a day or several times a day according to the dose desired. Generally a human adult will be administered from 0.2 to 200 mgs. per day, for example, from 1 to 100 mgs.

If the composition of this invention is intended for the induction of anorexia the composition will normally be in the form of a solid unit dosage form which contains from 0.2 mg. to 100 mg. of active ingredient, for example, 1 mg. to 100 mg. of active ingredient.

If the composition of this invention is intended for mood modification such as anti-depressant effects, it is likely that it will be used as a solid unit dosage form which contains from 0.1 mg. to 50 mg. of active ingredient, for example, 0.2 mg. to 25 mg. of active ingredient.

In a further aspect this invention provides a method of suppressing appetite, which comprises administering an effective amount of a compound of this invention.

In a further aspect this invention provides a method of reducing depression, which comprises administering an effective amount of a compound of this invention.

The present invention also provides processes for the preparation of the compounds of this invention.

The compounds of the formula (I) may be prepared from the corresponding compound of the formula (IV):

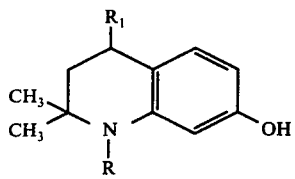
(IV)

and salts thereof wherein R and $R_1$ are as defined in relation to formula (I) by reaction with an etherifying agent such as that of the formula

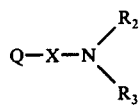

or an acid addition salt thereof wherein X, $R_2$ and $R_3$ are as defined in relation to formula (I) and Q is a readily displaceable group.

Suitable groups Q which are those which are readily displaced by nucleophilic groups and include the chlorine, bromine and iodine atoms and the hydroxyl group esterified by methane sulphonic, toluene sulphonic or like acid.

Particularly suitable groups Q include chlorine, bromine and iodine atoms and methanesulphonyl and toluenesulphonyl groups.

A preferred value for the group Q is chlorine.

The etherification reaction will normally be carried out in an inert solvent. Suitable solvents include hydrocarbons such as toluene or xylene, ethers such as dimethoxyethane, dimethoxypropane or tetrahydrofuran, ketones such as acetone, alcohols such as ethanol and other conventional solvents.

We have found a suitable solvent for this reaction to be dry tetrahydrofuran.

If desired the anion of the compound of formula (IV) may be produced before the etherification reaction or may be produced in situ by reaction with a base such as NaH or the like.

Generally any non-extreme temperature is used, but the reaction is substantially complete in a conveniently short time if an elevated temperature is used. For example, the reaction may be carried out at from about 0°–180° C, preferably in the region of 50°–120° C.

The compounds of formula (IV) may be prepared by the demethylation of the corresponding compound of the formula (V):

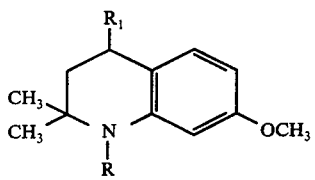
(V)

brought about by treatment with a strong acid such as hydrobromic acid.

A further method of preparation of the compounds of the formula (I) comprises the reaction of an amine $R_2R_3NH$ with a compound of the formula (VI):

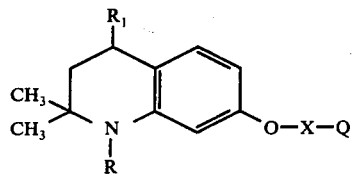
(VI)

wherein X, R, $R_1$, $R_2$ and $R_3$ are as defined in relation to formula (I); and Q is a readily displaceable group.

Suitable displaceable groups Q include those as defined in relation to formula (IV).

Such a reaction may take place at any non-extreme temperature, for example, 0°–180° C, but generally ambient or moderately elevated temperatures, for example, 12°–100° C are particularly suitable.

The displacement reaction normally takes place in an organic solvent such as ethanol, acetone, dimethylformamide, tetrahydrofuran, pyridine or the like. If a non-basic solvent is used it is often beneficial to include a tertiary base such as pyridine, triethylamine or the like to remove the acid HQ produced by the reaction.

A further method of preparing compounds of the formula (III) wherein $R_4$ is hydrogen is the reduction of a compound of the formula (VII):

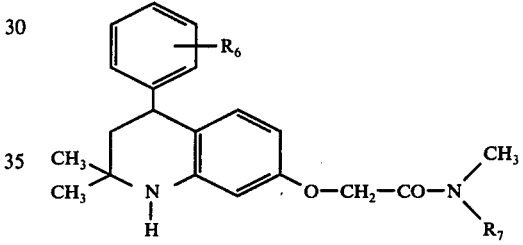
(VII)

wherein $R_6$ and $R_7$ are as defined in relation to formula (I) with a complex metal hydride capable of reducing amides to amines.

The present invention also provides a process: (a) for the preparation of those compounds of the formula (I) wherein $R_3$ is hydrogen, by the hydrogenation of the corresponding compound of the formula (I) wherein $R_3$ is a group removable by hydrogenolysis; (b) for the preparation of those compounds of the formula (I) wherein $R_2$ is methyl and/or $R_3$ is methyl, ethyl or benzyl, by the alkylation of a corresponding compound of the formula (I) wherein $R_2$ is hydrogen and $R_3$ is hydrogen, methyl, ethyl or benzyl; (c) for the preparation of those compounds of the formula (Ia):

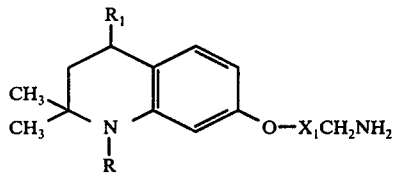
(Ia)

wherein $X_1$ is a group

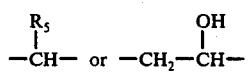

and R, R₁ and R₅ are as defined in relation to formula (I)

by the reduction of a compound of the formula (VIII):

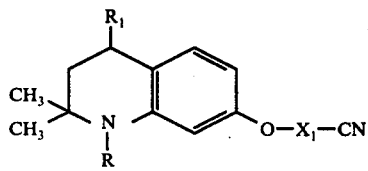

wherein X₁, R and R₁ are as defined in relation to formula (I) and (d) for the preparation of those compounds of the formula (IIb):

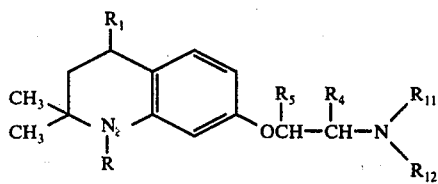

wherein R, R₁, R₄ and R₅ are as defined in relation to formula (I) R₁₁ is methyl; and R₁₂ is hydrogen, methyl or ethyl, the reduction by hydrogenation of a compound of the formula (IX):

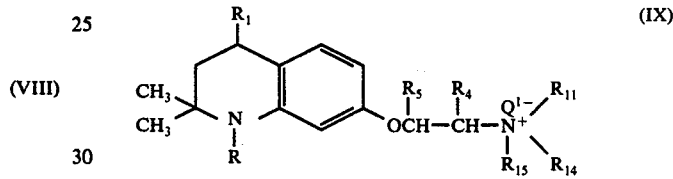

wherein R, R₁, R₄ and R₅ are as defined in relation to formula (I) R₁₁ is methyl; R₁₄ is methyl, ethyl or benzyl; and R₁₅ is benzyl.

The following examples are illustrative of the properties and preparation of the compounds of the present invention:

The following scheme illustrates the preparation of compounds of the invention wherein XNR₂R₃ = —CH₂—CH₂NMe₂ and R=Me.

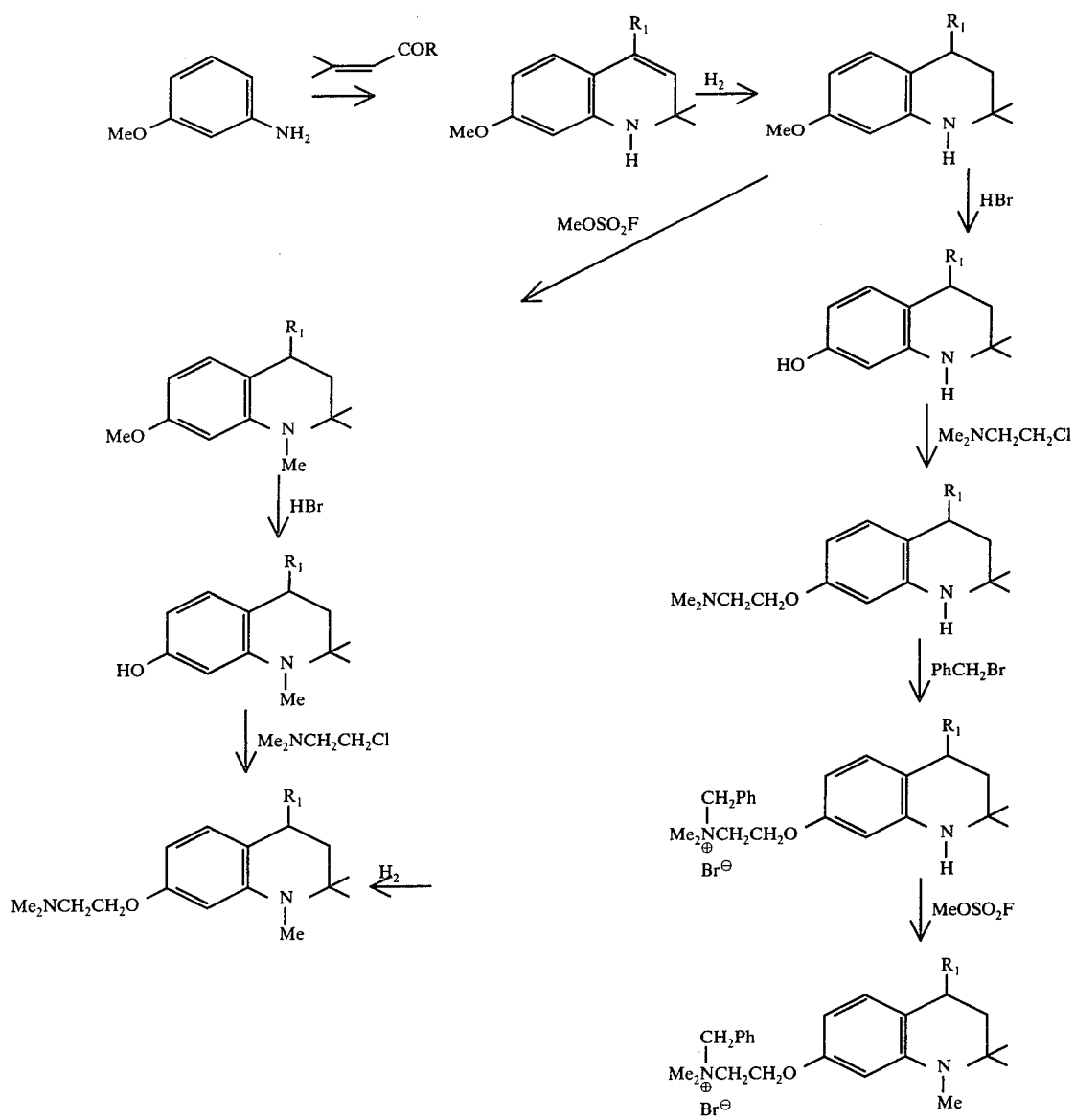

EXAMPLE 1(a)

Preparation of 2,2-dimethyl-7-methoxy-4-phenyl dihydroquinoline

Senecicephenone (19.3 g), m-anisidine (36.0 g) and p-toluene sulphonic acid (0.23 g) were refluxed in xylene (230 ml) in a Dean & Stank apparatus for 24 hours. The solvent was removed under reduced pressure, the residue dissolved in ether and extracted with 1N hydrochloric acid. The ether layer was dried (MgSO₄). Removal of the solvent under reduced pressure gave an oil (20 g) which was chromatographed on silica. Elution with dichloromethane gave 2-methyl-7-methoxy-2,4-diphenyldihydroquinoline followed by 2,4-dimethyl-7-methoxy-2-phenyldihydroquinoline. Continued elution with the same solvent gave the title compound slightly contaminated with 7-methoxy-2,2,4-trimethyldihydroquinoline (6 g).

Similarly prepared were:
2,2-dimethyl-7-methoxy-4-(4-trifluoromethylphenyl)-dihydroquinoline; 2,2-dimethyl-7-methoxy-4-(3-trifluoromethylphenyl)dihydroquinoline; and 2,2-dimethyl-7-methoxy-4-(4-chlorophenyl)dihydroquinoline.

EXAMPLE 1(b)

Preparation of 2,2-dimethyl-7-methoxy-4-phenyl tetrahydroquinoline 2,2-dimethyl-7-methoxy-4-phenyl dihydroquinoline (contaminated with 2,2,4-trimethyl compound) [60 g] was hydrogenated with 10% Pd/C (1.4 g) in ethanolacetic acid (200 ml). The reaction mixture was filtered through 'Mgflo' and the solvent removed under reduced pressure to give the title compound slightly contaminated with the trimethyl isomer (5 g).

Similarly prepared were:
2,2-dimethyl-7-methoxy-4-(4-trifluoromethylphenyl)-tetrahyroquinoline; 2,2-dimethyl-7-methoxy-4-(3-trifluoromethylphenyl)tetrahydroquinoline; and 2,2-dimethyl-7-methoxy-4-(4-chlorophenyl)tetrahydroquinoline (using Pt as catalyst).

EXAMPLE 1(c)

Preparation of 2,2-dimethyl-7-hydroxy-4-phenyl tetrahydroquinoline 2,2-dimethyl-7-methoxy-4-phenyl tetrahydroquinoline (slightly contaminated with 2,2,4-trimethyl compound) [5 g] was dissolved in glacial acetic acid (20 ml) and 48% hydrobromic acid (72 ml) added. The solution was boiled under reflux for 2 hours. The reaction mixture was poured into water, made basic with solid sodium bicarbonate and extracted with chloroform. The organic layers were dried (MgSO$_4$). Removal of the solvent under reduced pressure gave the title phenol as a foam (4.7 g, contaminated with the 2,2,4-trimethyl phenol).

Similarly prepared were:
2,2-dimethyl-7-hydroxy-4-(4-trifluoromethylphenyl)-tetrahydroquinoline m.p. 141.5° (petrol); 2,2-dimethyl-7-hydroxy-4-(3-trifluoromethylphenyl)tetrahydroquinoline and 2,2-dimethyl-7-hydroxy-4-(4-chlorophenyl)tetrahydroquinoline.

EXAMPLE 1(d)

Preparation of 2,2-dimethyl-7-dimethylaminoethoxy4-phenyltetrahydroquinoline dihydrochloride Sodium hydride (0.2 g of an 80% dispersion in oil) was added to 2,2-dimethyl-7-hydroxy-4-phenyltetrahydroquinoline (0.7 g) in dry tetrahydrofuran (40 ml). Dimethylaminoethyl chloride (0.3 g) and sodium iodide (trace) were added and the mixture boiled under reflux for 30 hours. Water was added and the reaction mixture extracted with ether and the combined ether layers dried (MgSO$_4$). Removal of the solvent under reduced pressure gave an oil (1.1. g) which was chromatographed on alumina (40 g). Elution with 1:1 ether/petrol (40-60) gave a clear oil (0.7 g). Treatment of this with ethereal hydrogen chloride gave the title compound (0.63 g) m.p. 136°-9°.

Similarly prepared were:
2,2-dimethyl-7-dimethylaminoethoxy-4-(3-trifluoromethylphenyl)tetrahydroquinoline dihydrochloride m.p. 125°-135°; 2,2-dimethyl-7-dimethylaminoethoxy-4-(4-trifluoromethylphenyl-tetrahydroquinoline dihydrochloride m.p. 141°-8°; and 2,2-dimethyl-7-dimethylaminoethoxy-4-(4-chlorophenyl)tetrahydroquinoline dihydrochloride m.p. 139°-143°.

EXAMPLE 2(a)

Preparation of 7-methoxy-4-(3-trifluoromethylphenyl)1,2,2-trimethyl tetrahydroquinoline Methyl fluorosulphonate (0.9 ml) was added to a solution of 2,2-dimethyl-7-methoxy-4-(3-trifluoromethylphenyl) tetrahydroquinoline (1.5 g) [as prepared in Example 1(b)] in chloroform (20 ml). The solution was boiled under reflux for 3 hours and left to stand for 16 hours. Sodium hydroxide solution (1N, 20 ml) was added, the layers separated and the aqueous layer extracted with chloroform. The combined organic layers were dried (MgSO$_4$). Removal of the solvent under reduced pressure gave an oil which was chromatographed on alumina (60 g). Elution with ether/petrol (1:9) gave an oil (0.7 g), the spectroscopic properties of which were compatible with the title compound.

EXAMPLE 2(b)

Preparation of 7-hydroxy-4-(3-trifluoromethylphenyl)-1,2,2-trimethyl tetrahydroquinoline 7-methoxy-4-(3-trifluoromethylphenyl)-1,2,2-trimethyl tetrahydroquinoline (0.7 g) was dissolved in a mixture of 48% hydrobromic acid (20 ml) and glacial acetic acid (6 ml) and the solution boiled under reflux for 11/2 hours. The reaction mixture was poured into water, solid sodium bicarbonate added until basic and the solution extracted with chloroform. The combined organic layers were dried (MgSO$_4$). Removal of the solvent under reduced pressure gave a purple-white foam (0.68 g), the spectroscopic properties of which were compatible with the title compound.

EXAMPLE 2(c)

Preparation of 7-dimethylaminoethoxy-4-(3-trifluoromethylphenyl)-1,2,2-trimethyl tetrahydroquinoline dihydrobromide Sodium hydride (0.1 g) was added to 7-hydroxy-4-(3-trifluoromethylphenyl)-1,2,2-trimethyltetrahydroquinoline (0.68 g) in dry tetrahydrofuran (50 ml). Dimethylaminoethyl chloride (0.3 g) and sodium iodide (0.3 g) were added and the mixture was boiled under reflux for 18 hours. The solvent was removed under reduced pressure, water added to the residue and the solution extracted with ether. The combined organic layers were dried (MgSO$_4$). Removal of the solvent under reduced pressure gave an oil which was chromatographed on alumina (30 g). Elution with ether gave a light-yellow oil (0.11 g). Further chromatography on an alumina thick layer plate gave the title compound (free base). N.m.r. (CDCl$_3$)$\tau$: 8.8 (3H, s); 8.7 (3H, s); 8.4-7.29 (2H, m); 7.75 (6H, s); 7.35 (2H, t, J=6Hz); 7.2 (3H, s); 6.0 (2H, t, J=6Hz); 6.0 (1H); 4.0-3.6 (3H, m); 2.65-2.45 (4H, m).

Treatment with ethereal hydrogen bromide gave the title compound m.p. 133°-135°. N.m.r. (CDCl$_3$)$\tau$: 8.35 (3H, s); 8.3 (3H, s); 7.95-7.65 (2H, m); 6.95 (6H, broad s); 6.75 (3H, s); 5.25 (2H, m); 5.4 (3H, m); 3.15-2.25 (7H, m); −1.0 (broad).

EXAMPLE 3(a)

Preparation of 7-(N-benzyldimethylaminoethoxy)-2,2-dimethyl-4-phenyl tetrahydroquinoline bromide A mixture of benzyl bromide (0.2 g) and 2,2-dimethyl7-dimethylaminoethoxy-4-phenyl tetrahydroquinoline (0.6 g) [as prepared in example 1(d)] in dry ether (5 ml) was left at −5° C for 50 hours. The precipitate was filtered and washed several times with ether to give the title compound (0.1 g).

EXAMPLE 3(b)

Preparation of 7-(N-benzyldimethylaminoethoxy)-4-phenyl-1,2,2-trimethyl tetrahydroquinoline bromide Methyl fluorosulphonate (0.1 ml) was added to a solution of 7-(N-benzyldimethylaminoethoxy)2,2-dimethyl-4-phenyl tetrahydroquinoline bromide (0.1 g) in chloroform (5 ml) and the solution left to stand for 10 minutes. The reaction mixture was poured into sodium hydroxide solution (1N), extracted with chloroform and the organic layers dried (MgSO$_4$). Removal of the solvent under reduced pressure gave an oil, the n.m.r. spectrum of which was compatible with the title compound.

EXAMPLE 3(c)

Preparation of 7-dimethylaminoethoxy-4-phenyl-1,2,2-trimethyl tetrahydroquinoline 10% palladium on charcoal (200 mg) was added to a solution of 7-(N-benzyldimethylaminoethoxy)-4-phenyl-1,2,2-trimethyl tetrahydroquinoline bromide (∼100 mg) in ethanol (20 ml) and the mixture hydrogenated. The reaction mixture was filtered through 'Mgflo' and the solvent removed under reduced pressure. The residue was taken up in chloroform and shaken with sodium hydroxide solution (1N). The layers were separated, the organic layer dried and the solvent removed under reduced pressure to give an oil which was chromatographed on an alumina thich layer plate to give the title compound, n.m.r. (CDCl$_3$)τ: 8.75 (3H, s); 8.7 (3H, s); 8.4–7.9 (2H, m); 7.7 (6H, s); 7.3 (2H, t, J=6Hz); 7.15 (3H, s); 5.95 (2H, t, J=6Hz); 5.95 (1H, m); 3.9–3.4 (3H, m); 3.7 (5H, s).

We claim:

1. A compound of the formula (II):

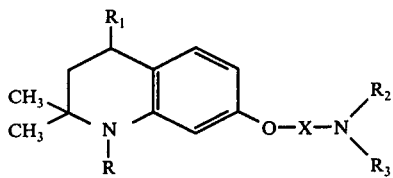

or a pharmaceutically acceptable acid addition salt thereof wherein X is

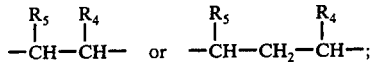

R is hydrogen, methyl or ethyl; R$_1$ is phenyl, naphthyl or phenyl substituted by a member selected from the group consisting of fluorine, chlorine, bromine, methyl, methoxy and trifluoromethyl; R$_2$ is hydrogen or methyl; R$_3$ is hydrogen, methyl, ethyl or benzyl; R$_4$ is hydrogen or methyl; and R$_5$ is hydrogen or methyl.

2. A compound according to claim 1 of the formula (III);

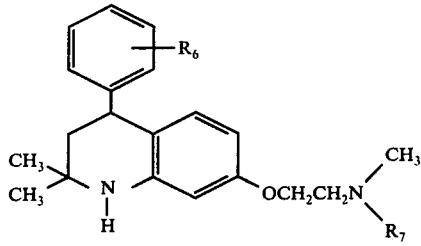

wherein R$_6$ is hydrogen, fluorine, chlorine or trifluoromethyl; and R$_7$ is hydrogen or methyl.

3. A compound according to claim 2 wherein R$_6$ is 3- or 4-trifluoromethyl.

4. A compound according to claim 2 wherein R$_7$ is methyl.

5. A compound according to claim 1 in the form of a salt selected from the group consisting of citrate, acetate, propionate, benzoate, lactate, tartrate, mandelate, succinate, oleate, glutarate, gluconate, methanesulphonate, toluenesulphonate, sulphate, phosphate, hydrobromide and hydrochloride.

6. The compound according to claim 1 which is 2,2-dimethyl-7-dimethylaminoethoxy-4-(3-trifluoromethylphenyl)tetrahydroquinoline dihydrochloride.

7. The compound according to claim 1 which is 2,2-dimethyl-7-dimethylaminoethoxy-4-(4-trifluoromethylphenyl)tetrahydroquinoline dihydrochloride.

8. The compound according to claim 1 which is 2,2-dimethyl-7-dimethylaminoethoxy-4-phenyltetrahydroquinoline dihydrochloride.

9. The compound according to claim 1 which is 2,2-dimethyl-7-dimethylaminoethoxy-4-(4-chlorophenyl)-tetrahydroquinoline dihydrochloride.

* * * * *